US012653484B2

(12) United States Patent     (10) Patent No.: US 12,653,484 B2

Suzuki et al.     (45) Date of Patent: Jun. 16, 2026

---

(54) RADIOGRAPHIC IMAGING APPARATUS, RADIOGRAPHIC IMAGING SYSTEM, METHOD FOR CONTROLLING RADIOGRAPHIC IMAGING APPARATUS, AND COMPUTER-READABLE RECORDING MEDIUM

(71) Applicant: CANON KABUSHIKI KAISHA, Tokyo (JP)

(72) Inventors: Kai Suzuki, Kanagawa (JP); Akira Tsukuda, Tokyo (JP); Yuichi Naito, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 18/417,531

(22) Filed: Jan. 19, 2024

(65) Prior Publication Data

US 2024/0148352 A1    May 9, 2024

Related U.S. Application Data

(63) Continuation of application No. PCT/JP2022/028509, filed on Jul. 22, 2022.

(30) Foreign Application Priority Data

Jul. 30, 2021    (JP) ................................. 2021-125345

(51) Int. Cl.
*A61B 6/00*     (2024.01)

(52) U.S. Cl.
CPC .................................... *A61B 6/547* (2013.01)

(58) Field of Classification Search
CPC ............................... A61B 6/587; A61B 6/547
See application file for complete search history.

(56) References Cited

U.S. PATENT DOCUMENTS

| | | | | |
|---|---|---|---|---|
| 6,092,928 | A * | 7/2000 | Mattson | A61B 6/583 |
| | | | | 378/207 |
| 7,744,279 | B2 * | 6/2010 | Heath | G03B 42/02 |
| | | | | 378/197 |
| 10,743,822 | B2 * | 8/2020 | Simon | A61B 6/465 |
| 12,369,878 | B2 * | 7/2025 | Komasaka | A61B 6/4233 |
| 2011/0311030 | A1 * | 12/2011 | Grzeda | A61B 6/527 |
| | | | | 378/162 |
| 2015/0190104 | A1 * | 7/2015 | Exelmans | A61B 6/563 |
| | | | | 378/96 |
| 2016/0252366 | A1 | 9/2016 | Park | |

FOREIGN PATENT DOCUMENTS

| | | |
|---|---|---|
| CN | 105931214 A | 9/2016 |
| CN | 107981878 A | 5/2018 |
| CN | 109391767 A | 2/2019 |
| EP | 3235430 A1 | 10/2017 |
| JP | 2015023915 A | 2/2015 |
| JP | 2018007923 A | 1/2018 |

\* cited by examiner

*Primary Examiner* — Dani Fox

(74) *Attorney, Agent, or Firm* — Canon U.S.A., Inc. IP Division

(57) ABSTRACT

A radiographic imaging apparatus according to the present invention includes an orientation measurement unit configured to measure information about an orientation of the radiographic imaging apparatus, wherein the orientation measurement unit performs correction of an output value of the orientation measurement unit based on an operation of radiographic imaging.

16 Claims, 5 Drawing Sheets

RADIOGRAPHIC IMAGING APPARATUS, RADIOGRAPHIC IMAGING SYSTEM, METHOD FOR CONTROLLING RADIOGRAPHIC IMAGING APPARATUS, AND COMPUTER-READABLE RECORDING MEDIUM

CROSS-REFERENCE TO RELATED APPLICATIONS

This application is a Continuation of International Patent Application No. PCT/JP2022/028509, filed Jul. 22, 2022, which claims the benefit of Japanese Patent Application No. 2021-125345, filed Jul. 30, 2021, both of which are hereby incorporated by reference herein in their entirety.

BACKGROUND OF THE INVENTION

Field of the Invention

The present invention relates to a radiographic imaging apparatus, a radiographic imaging system, a method for controlling the radiographic imaging apparatus, and a computer-readable recording medium.

Background Art

Flat panel detectors (FPDs) formed using semiconductor materials are widely used as radiation detectors for use in medical image diagnosis or non-destructive examination using radiation such as X-rays. Radiographic imaging apparatuses using a combination of a radiation detector described above and a radiation generating apparatus that generates radiation have been used.

As a function of the foregoing radiographic imaging apparatuses, a function of assisting in alignment of an irradiation field of radiation emitted from the radiation generating apparatus and an incident surface of the radiation detector by calculating orientations of the radiation generating apparatus and the radiation detector and displaying the calculated orientations has been put into practical use.

As a method for calculating orientations of the radiation generating apparatus and the radiation detector, the radiation generating apparatus and the radiation detector are each provided with an acceleration sensor or a gyro sensor, and orientations of the radiation generating apparatus and the radiation detector are calculated based on acceleration values output by the acceleration sensors and angular velocity values output by the gyro sensors.

For example, Patent Literature 1 discusses a radiographic imaging system including an assistance control unit configured to perform imaging assistance processing based on values from a tilt angle detection unit provided to a radiographic imaging apparatus and using an acceleration sensor or a gyro sensor and a tilt angle detection unit provided to a radiation generating apparatus and using an acceleration sensor or a gyro sensor.

CITATION LIST

Patent Literature

PTL 1: Japanese Patent Application Laid-Open No. 2018-007923

Since output values of an acceleration sensor and a gyro sensor contain errors, it is sometimes difficult to calculate a correct orientation of a radiographic imaging apparatus using the output values of the sensors.

SUMMARY OF THE INVENTION

The present invention is directed to enhancing accuracy of alignment of a radiation generating apparatus and a radiographic imaging apparatus with each other by correcting output values that are output from an acceleration sensor or a gyro sensor used as an orientation measurement unit of the radiographic imaging apparatus and contain errors.

Issues to be solved by the present invention are solved by a radiographic imaging apparatus including an orientation measurement unit configured to measure information about an orientation of the radiographic imaging apparatus, wherein the orientation measurement unit performs correction of an output value of the orientation measurement unit based on an operation of radiographic imaging.

Further features of the present invention will become apparent from the following description of exemplary embodiments with reference to the attached drawings.

DESCRIPTION OF THE EMBODIMENTS

Figure 1:
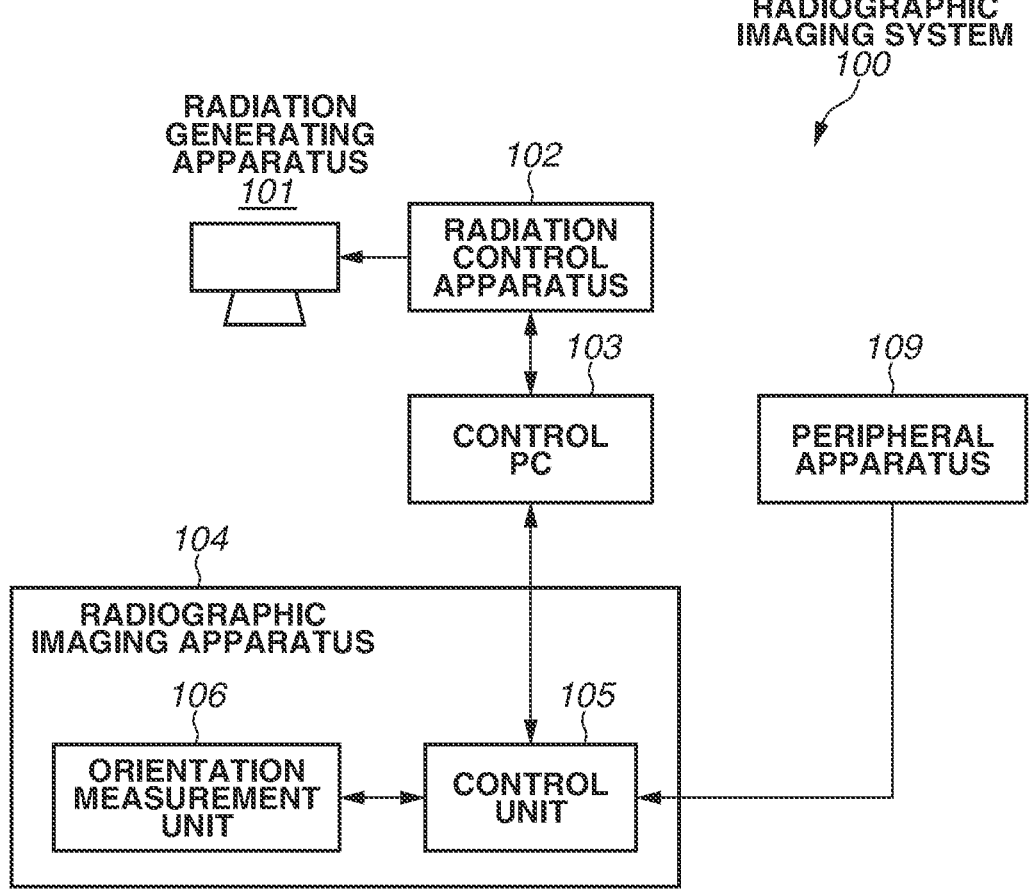
FIG. 1 illustrates an example of a configuration of a radiographic imaging system according to a first exemplary embodiment.

Various exemplary embodiments of the present invention will be described below with reference to the attached drawings. It is to be noted that the exemplary embodiments described below are not intended to limit the scope of the claimed invention. While a plurality of features according to the exemplary embodiments is described below, not all of the plurality of features are always essential to the invention, and the plurality of features can be combined as desired. Furthermore, in the attached drawings, components that correspond or are similar to each other are given the same reference numeral, and redundant descriptions thereof are omitted. Further, the term "radiation" typically refers to X-rays but can also include other rays such as α-rays, β-rays, γ-rays, particle rays, and cosmic rays.

First Exemplary Embodiment

A method for accurately calculating orientation information about, for example, a radiographic imaging apparatus that includes an acceleration sensor as an orientation measurement unit by removing offset components of the acceleration sensor according to the present exemplary embodiment will be described below. While the acceleration sensor is used as the orientation measurement unit according to the present exemplary embodiment described below, this is not a limitation, and a gyro sensor, for example, can be used as the orientation measurement unit.

First, a configuration of a radiographic imaging system according to the present exemplary embodiment will be described below with reference to FIG. 1. FIG. 1 is a schematic diagram illustrating a configuration of a radiographic imaging system 100. The radiographic imaging system 100 includes a radiation generating apparatus 101, a radiation control apparatus 102, a control personal computer (control PC) 103, a radiographic imaging apparatus 104, and a peripheral apparatus 109.

The radiation generating apparatus 101 emits radiation to a subject. The radiation generating apparatus 101 includes a tube configured to generate radiation, a collimator configured to define a beam divergence angle of the generated radiation, and a radiation dosimeter attached to the collimator.

The radiation control apparatus 102 controls the radiation generating apparatus 101 based on an imaging condition input by a user via the control PC 103. Before the radiation generating apparatus 101 emits radiation, the radiation control apparatus 102 transmits an irradiation permission signal to the radiographic imaging apparatus 104 to be irradiated with the radiation. After receiving an irradiation permission response to the irradiation permission signal from the radiographic imaging apparatus 104, the radiation generating apparatus 101 emits radiation to the radiographic imaging apparatus 104.

The control PC 103 can use a general-purpose personal computer. Specifically, a general-purpose computer formed by hardware including a central processing unit (CPU), a main storage device such as a dynamic random access memory (DRAM), and an auxiliary storage device such as a solid state drive (SSD) or a hard disk drive (HDD) and a general-purpose display are included. The user inputs an imaging condition instruction to the radiation control apparatus 102 as described above and checks a radiographic image displayed on the display using the control PC 103.

The radiographic imaging apparatus 104 includes a scintillator configured to convert radiation into light and photoelectric conversion elements arranged in a two-dimensional matrix and configured to convert light from the scintillator into charge. The radiographic imaging apparatus 104 generates an image based on emitted radiation. The generated radiographic image is transmitted to the control PC 103. Further, the radiographic imaging apparatus 104 transmits detected radiation dose information to the radiation control apparatus 102.

The radiographic imaging apparatus 104 includes a control unit 105 and an orientation measurement unit 106. The control unit 105 forms radiographic images by processing signals from the photoelectric conversion elements and controls the radiographic imaging apparatus 104 for performing radiographic imaging. Further, the control unit 105 has a plurality of operation modes and operates the radiographic imaging apparatus 104 in an operation mode suitable for each radiographic imaging operation flow. Details of the operation modes will be described below.

The orientation measurement unit 106 measures orientation information about the radiographic imaging apparatus 104 and generates output values. According to the present exemplary embodiment, the orientation measurement unit 106 is a three-axis acceleration sensor and outputs an acceleration in each axial direction of three axes (X-axis, Y-axis, Z-axis) of a Cartesian coordinate system.

The control unit 105 has a function of calculating an orientation of the radiographic imaging apparatus 104 based on the output values generated by the orientation measurement unit 106. The orientation refers to an angle with respect to each of the three axes (X-axis, Y-axis, Z-axis) of the Cartesian coordinate system.

Orientation calculation results are used in determining whether to perform correction on the output values of the orientation measurement unit 106. Further, the calculation results are also transmitted to the control PC 103 to use the calculation results to display a current orientation of the radiographic imaging apparatus 104 on the display. The user can check the orientation of the radiographic imaging apparatus 104 displayed on the display of the control PC 103 in aligning the radiation generating apparatus 101 and the radiographic imaging apparatus 104 with each other for radiographic imaging, and this enables prompt and highly-accurate alignment.

The peripheral apparatus 109 can be, for example, a charging apparatus that can charge the radiographic imaging apparatus 104 or an upright or recumbent imaging table. The peripheral apparatus 109 in any of these forms stabilizes the radiographic imaging apparatus 104 in a specific orientation in a case where the radiographic imaging apparatus 104 is connected.

While FIG. 1 illustrate an example of a case where the radiation generating apparatus 101 and the radiographic imaging apparatus 104 are connected together via the control PC 103, this is not a limiting case, and the radiation generating apparatus 101 and the radiographic imaging apparatus 104 can be connected together via, for example, a switching hub. Further, the radiation generating apparatus 101 and the radiographic imaging apparatus 104 can be wire-connected together using cables or can be connected together wirelessly using a publicly-known technology.

By connecting the radiation generating apparatus 101 and the radiographic imaging apparatus 104 together, it becomes possible to perform synchronous imaging by synchronizing imaging timings and performing imaging. Further, it is also possible to perform non-synchronous imaging by detecting radiation emission and then performing imaging by the radiographic imaging apparatus 104 without synchronizing the radiation generating apparatus 101 and the radiographic imaging apparatus 104 with each other.

Figure 2A:
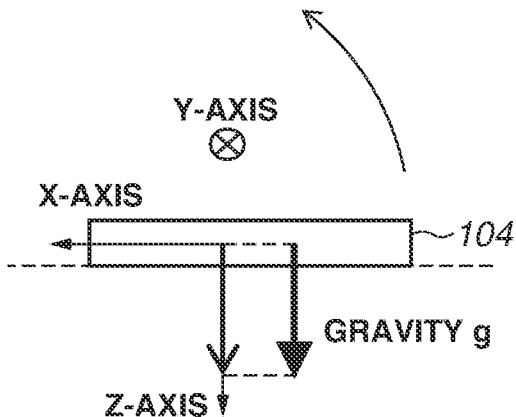
FIG. 2A is a schematic diagram illustrating a method for calculating an orientation of the radiographic imaging apparatus according to the first exemplary embodiment.
Figure 2B:
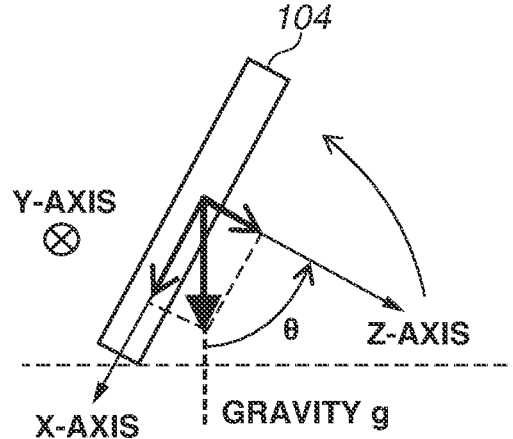
FIG. 2B is a schematic diagram illustrating a method for calculating an orientation of the radiographic imaging apparatus according to the first exemplary embodiment.

Next, a method for calculating an orientation (angle) of the radiographic imaging apparatus 104 using the acceleration sensor, which is an example of the orientation measurement unit 106, will be described below with reference to FIGS. 2A and 2B. FIGS. 2A and 2B are schematic diagrams illustrating a method for calculating an orientation (angle) of the radiographic imaging apparatus 104 based on outputs of the acceleration sensor. A case where one side of an X-ray imaging apparatus arranged with a Z-axis downward is lifted and stabilized in an orientation will be described below as an example. The Z-axis is an axis perpendicular to a radiation exposure surface, and two axes meeting at a right angle in the radiation exposure surface are referred to as an X-axis and a Y-axis.

In a case where the radiographic imaging apparatus 104 is rotated around the Y-axis and is stabilized so that an angle $\theta$ is formed between the Z-axis and the gravity, the following equations hold:

$$ax = g \times \sin(\theta) \qquad \text{(equation 1); and}$$

$$az = g \times \cos(\theta) \qquad \text{(equation 2),}$$

where ax and az are respectively an X-axis output and a Z-axis output of the acceleration sensor.

In the foregoing equations, g is a gravity acceleration.

Next, an orientation $\theta$ of the X-ray imaging apparatus is calculated by $$\theta=\tan^{-1}(ax/az) \qquad \text{(equation 3)}.$$

In a case where the radiographic imaging apparatus 104 is situated parallel to the ground as illustrated in FIG. 2A at the start of operation, the gravity g does not act in the X-direction but acts entirely in the Z-direction, so that the outputs ax and az of the acceleration sensor are respectively 0 g and +1 g. In a case where the radiographic imaging apparatus 104 is rotated from this state around the Y-axis as illustrated in FIG. 2B, the angle $\theta$ of the radiographic imaging apparatus 104 is calculated based on the values of ax and az.

Offset components contained in the output values of the acceleration sensor will be described below. Hereinafter, $ax_{off}$ and $az_{off}$ denote offset components of the acceleration sensor in the X- and Z-axis directions, respectively. By transforming equation 3 to include $ax_{off}$ and $az_{off}$, equation 4 below is obtained.

$$\theta=\tan^{-1}((ax+ax_{off})/az+az_{off}) \qquad \text{(equation 4)}.$$

For example, in a case where a true $\theta$ is 0° and the X- and Z-axis components each contain a 50-mg offset component, the output values of the acceleration sensor are ax=+0.05 g and az=+1.05 g, and a value $\theta$ of about 3° is obtained based on equation 4.

While an error in a calculated angle in a case where a 50-mg offset component is contained is calculated as an example, a general acceleration sensor contains offset components ranging from several tens mg to several hundreds mg. Thus, for accurate calculations of an orientation of the radiographic imaging apparatus 104, the offset components are to be removed properly. An example of a method for removing offset components of the acceleration sensor is a method in which an offset component is calculated by sampling an output value of the acceleration sensor a plurality of times and obtaining an addition average of the sampled values and the calculated offset component is subtracted from an output value.

Figure 3:
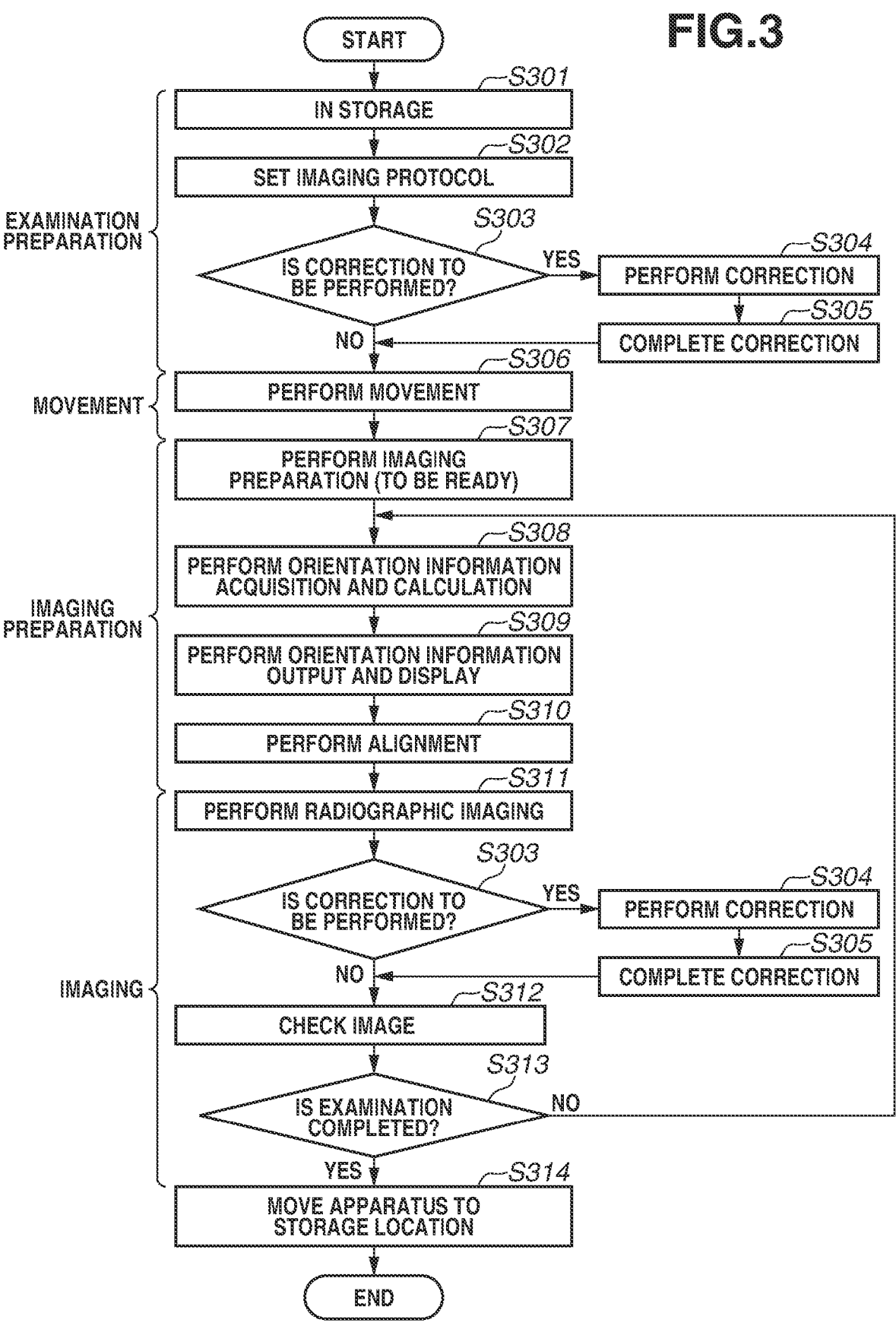
FIG. 3 is a flowchart illustrating an examination flow according to the first exemplary embodiment.

Next, an examination flow in a case where the acceleration sensor is used as the orientation measurement unit 106 of the radiographic imaging apparatus 104 will be described below with reference to FIG. 3. As illustrated in FIG. 3, the examination flow is divided into the following four phases, examination preparation, movement, imaging preparation, and imaging.

<Examination Preparation>

Before the start of an examination, the radiographic imaging apparatus 104 is in a state of being placed on the charging apparatus or being in storage at a predetermined storage location (step 301). Then, as the examination preparation, a doctor or a laboratory technologist as a user sets, for the radiographic imaging apparatus 104 to be used, imaging protocols for scheduled examinations from the control PC 103 (step 302).

<Movement>

After the examination preparation is completed, the radiographic imaging apparatus 104 to be used is moved from the storage location to an examination location (step 306). As a method for the movement, the radiographic imaging apparatus 104 is placed in a pocket of a rounds trolley for the radiographic imaging apparatus 104 and conveyed, or the doctor or the laboratory technologist as a user carries the radiographic imaging apparatus 104 by hand.

<Imaging Preparation>

After the radiographic imaging apparatus 104 arrives at the examination location, the imaging preparation is performed. Specific operations are an operation of changing the radiographic imaging apparatus 104 to an imaging preparation state (step 307) and an operation of aligning the radiation generating apparatus 101, the radiographic imaging apparatus 104, and a subject with each other based on examination details (step 310).

<Imaging>

After the alignment of the radiation generating apparatus 101 and the radiographic imaging apparatus 104 with each other is completed, the radiation generating apparatus 101 emits radiation to the subject and the radiographic imaging apparatus 104 at the press of an exposure switch by the user, and radiographic imaging is performed (step 311).

The user checks a captured image displayed on the control PC 103 and checks for any issues in the imaging (step 312), and in a case where all the scheduled examinations are completed, the radiographic imaging apparatus 104 is returned to the original storage location (step 314). In a case where the captured image is unsuitable for diagnosis or there is still a remaining scheduled examination, the processing returns to the imaging preparation phase, and the alignment of the radiation generating apparatus 101, the radiographic imaging apparatus 104, and the subject with each other is performed again for the next imaging. The phases from the imaging preparation to the imaging are repeated as described above until all the scheduled examinations are completed.

In the foregoing examination flow, the phase in which the user uses orientation information about the radiographic imaging apparatus 104 is the imaging preparation phase. There are a method in which orientation information is periodically output to a screen of the control PC 103 and a method in which orientation information is displayed on an interface such as a display provided to the radiation generating apparatus 101.

The removal of offset components contained as errors in the orientation measurement unit 106 is to be performed at a timing when the radiographic imaging apparatus 104 is stationary. According to the present exemplary embodiment, whether the radiographic imaging apparatus 104 is stationary is determined using the operation mode of the radiographic imaging apparatus 104 and a context of an operation performed on the radiographic imaging apparatus 104 by the user.

The radiographic imaging apparatus 104 has the plurality of operation modes. For example, "Power Off" is a mode in which the radiographic imaging apparatus 104 is not powered on. "Sleep" is a mode in which the radiographic imaging apparatus 104 is powered on but the photoelectric conversion elements are not driving. "Sleep to Ready" is a mode in which the photoelectric conversion elements start driving and the imaging preparation is performed. "Ready" is a mode in which the photoelectric conversion elements are driving and an irradiation permission signal from the radiation control apparatus 102 is awaited. "ExpReady" is a mode in which the radiographic imaging apparatus 104 recognizes an irradiation permission signal from the radiation control apparatus 102 and becomes ready for imaging.

An example of a method of determining whether the radiographic imaging apparatus 104 is stationary based on the operation mode of the radiographic imaging apparatus 104 and the operation context and removing offset components of the orientation measurement unit 106 in the examination flow illustrated in FIG. 3 will be described below.

At the time of step 301 in FIG. 3, the radiographic imaging apparatus 104 is in storage at the predetermined storage location (e.g., charging apparatus). Then, in step 302, the imaging protocol setting is performed by the user.

At the time of the imaging protocol setting, the radiographic imaging apparatus 104 is stationary at the predetermined storage location. At this time, the operation mode of the radiographic imaging apparatus 104 is "Sleep".

Specifically, the radiographic imaging apparatus 104 is stationary at the timing when the operation mode of the radiographic imaging apparatus 104 is "Sleep" and the imaging protocol setting is performed. Thus, this is a timing when the correction of errors contained in the output values of the orientation measurement unit 106 can be performed.

Thus, as step 303, whether to perform the correction of the output values of the orientation measurement unit 106 is determined by the control unit 105. The determination can be automatic. For example, it can be determined to perform the correction in a case where a predetermined period has passed since the last correction. Further, the determination can be manual based on whether a specific operation is performed on the control PC 103 or the radiographic imaging apparatus 104 by the user after the user is notified of the state of being ready for the correction. In a case where it is determined to perform the correction in step 303, the processing proceeds to step 304. In a case where the correction is not to be performed, the processing proceeds to step 306.

In a case where the correction of the output values of the orientation measurement unit 106 is to be performed in step 304, a warning is provided to warn the user not to move the radiographic imaging apparatus 104 during the correction. The warning is provided by, for example, displaying the warning on the display of the control PC 103 or by providing a notification using a notification unit such as a light emitting diode (LED) or a speaker of the radiographic imaging apparatus 104. After the correction is performed, the processing proceeds to step 305, and after the completion of the correction is confirmed, the processing proceeds to step 306.

In a case where the operation mode of the radiographic imaging apparatus 104 changes to Ready in step 307, the acceleration sensor that is the orientation measurement unit 106 acquires a value, and the value is calculated by the control unit 105 (step 308), followed by output and display of orientation information (step 309). The user performs alignment of the radiation generating apparatus 101 and the radiographic imaging apparatus 104 with each other based on the orientation information about the radiographic imaging apparatus 104 that is displayed on, for example, the control PC 103 (step 310).

After the alignment is completed, the exposure switch is pressed by the user, and the operation mode of the radiographic imaging apparatus 104 is changed to ExpReady, which is a state where radiation can be emitted. Then, the radiation generating apparatus 101 emits radiation to the radiographic imaging apparatus 104, and radiographic imaging is performed (step 311). After the imaging ends, the operation mode of the radiographic imaging apparatus 104 is changed to the Ready state. At this timing immediately after the imaging, the radiographic imaging apparatus 104 is stationary, so that the correction of the output values of the orientation measurement unit 106 can be performed. Thus, the above-described operations of steps 303 to 305 can be performed.

The captured image is transferred to the control PC 103 and displayed on the display of the control PC 103, and the user checks the radiographic image. In a case where the correction of the output values of the orientation measurement unit 106 is performed, the correction can be performed in parallel with the check on the captured image. After the check on the image, an examination completion determination is performed as step 313, and in a case where all the scheduled protocols are completed, the X-ray imaging apparatus is moved to the storage location in step 314, and the examination flow ends. In a case where there is still a remaining protocol, steps 308 to 313 are repeated until all the protocols are completed.

As described above, according to the present exemplary embodiment, the correction of the output values of the orientation measurement unit 106 is performed based on the operation context of the radiographic imaging. The correction is performed in a state where the radiographic imaging apparatus 104 is stationary. Whether the radiographic imaging apparatus 104 is stationary is determined by the control unit 105 by detecting the operation mode of the radiographic imaging apparatus 104 that the control unit 105 possesses and the context of the operation performed on the radiographic imaging apparatus 104.

For example, in the imaging preparation phase, the initiation of the correction of the output values of the orientation measurement unit 106 by the radiographic imaging apparatus 104 can be triggered in a case where the radiographic imaging apparatus 104 is in the Sleep state and the protocol setting is performed. Further, in the imaging phase, the initiation of the correction can be triggered in a case where the imaging is completed and the operation mode of the radiographic imaging apparatus 104 is changed from ExpReady to Ready.

The correction of the output values of the orientation measurement unit 106 can be performed automatically based on the determination by the control unit 105. Further, a notification that the control unit 105 determines that the correction can be performed can be provided to the user, and the user can determine whether to perform the correction and can manually perform the correction by operating an input unit such as the control PC 103.

Further, it is known that offset components contained as errors in the orientation measurement unit 106 vary depending on the use environment. For example, the offset components vary due to temperature effects. The use environment of the radiographic imaging apparatus 104 is diverse, and even in a case where, for example, the correction of the output values of the orientation measurement unit 106 is performed at the time of factory shipment, there remains a potential for temperature variation from an actual use environment such as a hospital. Further, even in a case where the correction is performed at the time of installation to a hospital, there remains a potential for temperature variation from the time of installation to the time of actual use. Even a slight environmental difference can decrease the accuracy of calculated orientation information, so that the correction is to be performed under conditions that are as close as possible to an actual use environment of the orientation information.

According to the present exemplary embodiment, the correction of the output values of the orientation measurement unit 106 is performed in an environment close to an actual use environment by performing the correction at one of the above-described timings, so that effects of offset components contained as errors in the output values of the orientation measurement unit 106 are reduced. This enables accurate calculations of orientation information about the radiographic imaging apparatus 104, so that the user can accurately perform the alignment of the radiation generating apparatus 101 and the radiographic imaging apparatus 104 with each other.

While the timing immediately after the imaging protocol setting is performed and the timing immediately after the radiographic image is acquired are described above as examples of the timing of performing the correction of the output values of the orientation measurement unit 106 according to the present exemplary embodiment, the timing is not limited to the examples. The correction of the output values of the orientation measurement unit 106 can be performed at any other timing when the radiographic imaging apparatus 104 is stationary.

Second Exemplary Embodiment

An example of a case of using the output values of the orientation measurement unit 106 in the determination of whether to perform the correction of the output values of the orientation measurement unit 106 according to the present exemplary embodiment will be described below.

In the case of using the three-axis acceleration sensor as the orientation measurement unit 106, the output values of the axes of the acceleration sensor are constant values in a case where the radiographic imaging apparatus 104 is stationary. Two methods for determining whether the radiographic imaging apparatus 104 is stationary will be described below as examples.

The first method is a method that uses a temporal variation (differential value $\Delta a$) of an output value a of the orientation measurement unit 106. The orientation measurement unit 106 transmits the output value a to the control unit 105. The control unit 105 calculates a temporal variation (differential value $\Delta a$) of the output value a and compares $\Delta a$ with a threshold th1. In a case where $\Delta a$ is less than the threshold th1, it is determined that the radiographic imaging apparatus 104 is stationary. In this case, the correction of the output values of the orientation measurement unit 106 is performed based on the following equation 5, $$a\text{out}=a-\Delta a \qquad \text{(equation 5).}$$

By subtracting the differential value $\Delta a$, which is the temporal variation of the output value a, from the output value a of the orientation measurement unit 106 as expressed by equation 5, an output value aout after the components that change over time are removed is obtained.

The second method is a method in which an orientation a0 of the radiographic imaging apparatus 104 at a time point is stored in advance in the control unit 105 and is used in the determination of whether the radiographic imaging apparatus 104 is stationary. The control unit 105 compares the output value a acquired by the orientation measurement unit 106 with the orientation a0 stored in the control unit 105, and in a case where the difference between the output value a and the orientation a0 is less than a threshold th2, there has been no change in orientation of the radiographic imaging apparatus 104 from the orientation a0.

Furthermore, in a case where the control unit 105 further determines that the temporal variation (differential value $\Delta a$) of the output value a of the orientation measurement unit 106 becomes less than the threshold th1, it is determined that there has been no change in orientation of the radiographic imaging apparatus 104 from the orientation stored in advance and that the radiographic imaging apparatus 104 is stationary. An output value aout after the components that do not change over time are removed in addition to the components that change over time is obtained by performing the correction of the output values of the orientation measurement unit 106 based on the following equation 6, $$a\text{out}=a0 \qquad \text{(equation 6).}$$

Storing various states in which the radiographic imaging apparatus 104 is stationary, such as a state in which the radiographic imaging apparatus 104 is in an upright position, a state in which the radiographic imaging apparatus 104 is in a recumbent position, and a state in which the radiographic imaging apparatus 104 is placed in the pocket of the rounds trolley, as the orientation a0 in the control unit 105 enables accurate removal of offset components contained in output acceleration values.

Figure 4:
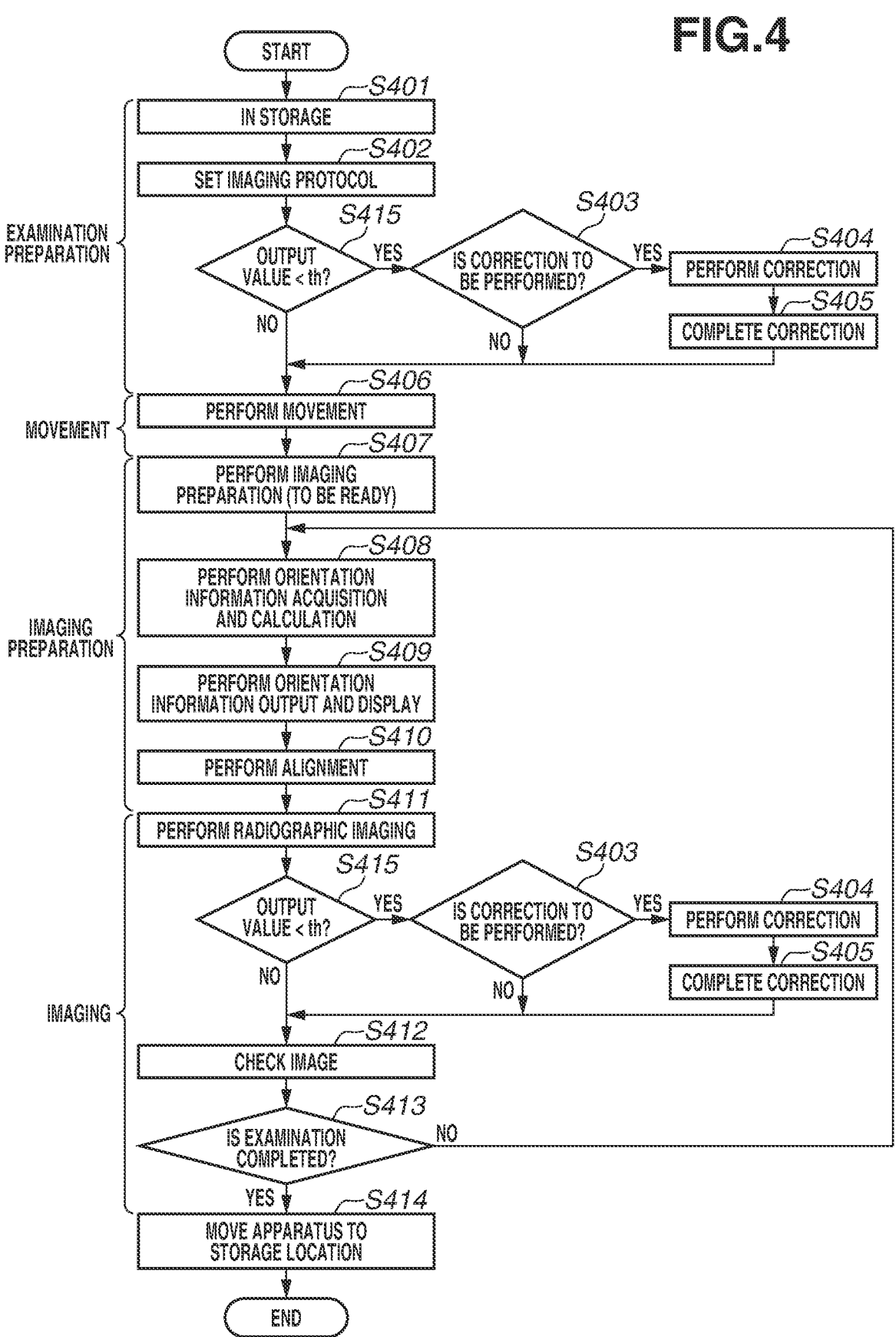
FIG. 4 is a flowchart illustrating an examination flow according to a second exemplary embodiment.

FIG. 4 illustrates an examination flow according to the present exemplary embodiment. Redundant descriptions of each step that corresponds to a step in FIG. 3 are omitted.

Steps 401 and 402 correspond to steps 301 and 302 in FIG. 3. In FIG. 4, at the timing immediately after the imaging protocol setting is performed in step 402, the operation mode of the radiographic imaging apparatus 104 is Sleep, and the radiographic imaging apparatus 104 is stationary. At this time, as next step 415, the output value a of the orientation measurement unit 106 is checked. This ensures that the radiographic imaging apparatus 104 is stationary during the correction.

In step 415, in a case where the radiographic imaging apparatus is determined as being stationary, the processing proceeds to step 403 of determining whether to perform the correction. In step 415, in a case where the radiographic imaging apparatus is determined as not being stationary, the processing does not proceed to the determination of whether to perform the correction but proceeds to step 406.

Steps 403 to 411 of radiographic imaging correspond to steps 303 to 311 in FIG. 3, so that redundant descriptions thereof are omitted.

After the radiographic imaging is performed in step 411 and the imaging is ended, the radiographic imaging apparatus is changed to the Ready state. At this timing immediately after the imaging, the radiographic imaging apparatus is also stationary, so that the check on the output values of the orientation measurement unit 106, which is described above, is performed as step 415.

In a case where the radiographic imaging apparatus is determined as being stationary by the above-described method, the processing proceeds to step 403 of determining whether to perform the correction, whereas in a case where the radiographic imaging apparatus is determined as not being stationary, the correction is not performed, and the processing proceeds to step 412 of performing an image check. Step 412 and subsequent steps correspond to step 312 and the subsequent steps according to the first exemplary embodiment, so that redundant descriptions thereof are omitted.

By the foregoing imaging flow, in a case where the radiographic imaging apparatus is detected as being stationary based on the output values of the orientation measurement unit 106, the correction of the output values of the orientation measurement unit 106 is performed. This reduces effects of offset components contained as errors in the output values of the orientation measurement unit 106. The reduction of the effects of the offset components enables accurate calculations of orientation information about the radiographic imaging apparatus 104, so that the user can accurately perform the alignment of the radiation generating apparatus 101 and the radiographic imaging apparatus 104 with each other.

While the timing immediately after the imaging protocol setting is performed and the timing immediately after the radiographic image is acquired are described above as examples of the timing of determining whether to perform the correction of the output values of the orientation measurement unit 106 according to the present exemplary embodiment as in the first exemplary embodiment, the timing is not limited to the examples. The correction can be performed at any timing when the radiographic imaging apparatus 104 is stationary.

Third Exemplary Embodiment

A method of accumulating the outputs of the orientation measurement unit 106, calculating a displacement amount from a reference position, and calculating a position of the radiographic imaging apparatus 104 or the distance between the radiation generating apparatus 101 and the radiographic imaging apparatus 104 according to the present exemplary embodiment will be described below.

As in the first and second exemplary embodiments, the radiographic imaging apparatus 104 includes a three-axis acceleration sensor as the orientation measurement unit. A method for calculating a position of the radiographic imaging apparatus 104 using the acceleration sensor will be described below.

By accumulating an output value a(t) of one axis of the acceleration sensor at time t from t=0 to a(t) with a time interval Δt by acquiring data n times (t=nΔt), a velocity v(t) at time t is calculated as expressed by equation 7 below, $$v(t)=v(0)+\Sigma a(k\Delta t)\Delta t(k=1 \text{ to } n) \qquad \text{(equation 7),}$$

where v(0) is an initial value of the velocity at t=0.

Furthermore, a position x(t) at time t can be expressed by equation 8 below, $$x(t)=x(0)+\Sigma v(k\Delta t)\Delta t(k=1 \text{ to } n) \qquad \text{(equation 8),}$$

where x(0) is an initial value of the position at t=0.

A known numerical integration method (trapezoidal rule, Simpson's rule) can be used to enhance the calculation accuracy.

A relative position of the radiographic imaging apparatus from an initial position is calculated by the above-described method. According to the present exemplary embodiment, the initial position of the radiographic imaging apparatus is a storage location in an examination room (specifically, a state of being connected to the charging apparatus as the peripheral apparatus in FIG. 1). Furthermore, in a case where a unit for acquiring a movement amount of the tube is also provided to the radiation generating apparatus (near the tube), a position of the tube in the examination room is also calculated similarly.

As the unit for acquiring a movement amount of the tube, an acceleration sensor can be included as in the radiographic imaging apparatus, and the position of the tube can be calculated based on outputs of the acceleration sensor. Further, the calculation can be performed based on displacement amounts of rails for running the radiation generating apparatus 101 that are stabilized in the room or a displacement amount of a motor for expanding and contracting the tube.

In general, the position at which the charging apparatus of the radiographic imaging apparatus is installed and the position at which the radiation generating apparatus is installed remain unchanged, so that the absolute coordinates of the charging apparatus of the radiographic imaging apparatus and the radiation generating apparatus in the examination room are considered to be known. Thus, the absolute coordinates in the room can be calculated based on the relative positions from the initial positions of the radiographic imaging apparatus and the tube.

In calculating the position of the radiographic imaging apparatus, the numerical integration is to be performed as described above. In the numerical integration, the output values of the acceleration sensor over the data acquisition time are added, so that offset components contained in the outputs of the acceleration sensor become an influence of errors in calculating positional information.

Figure 5:
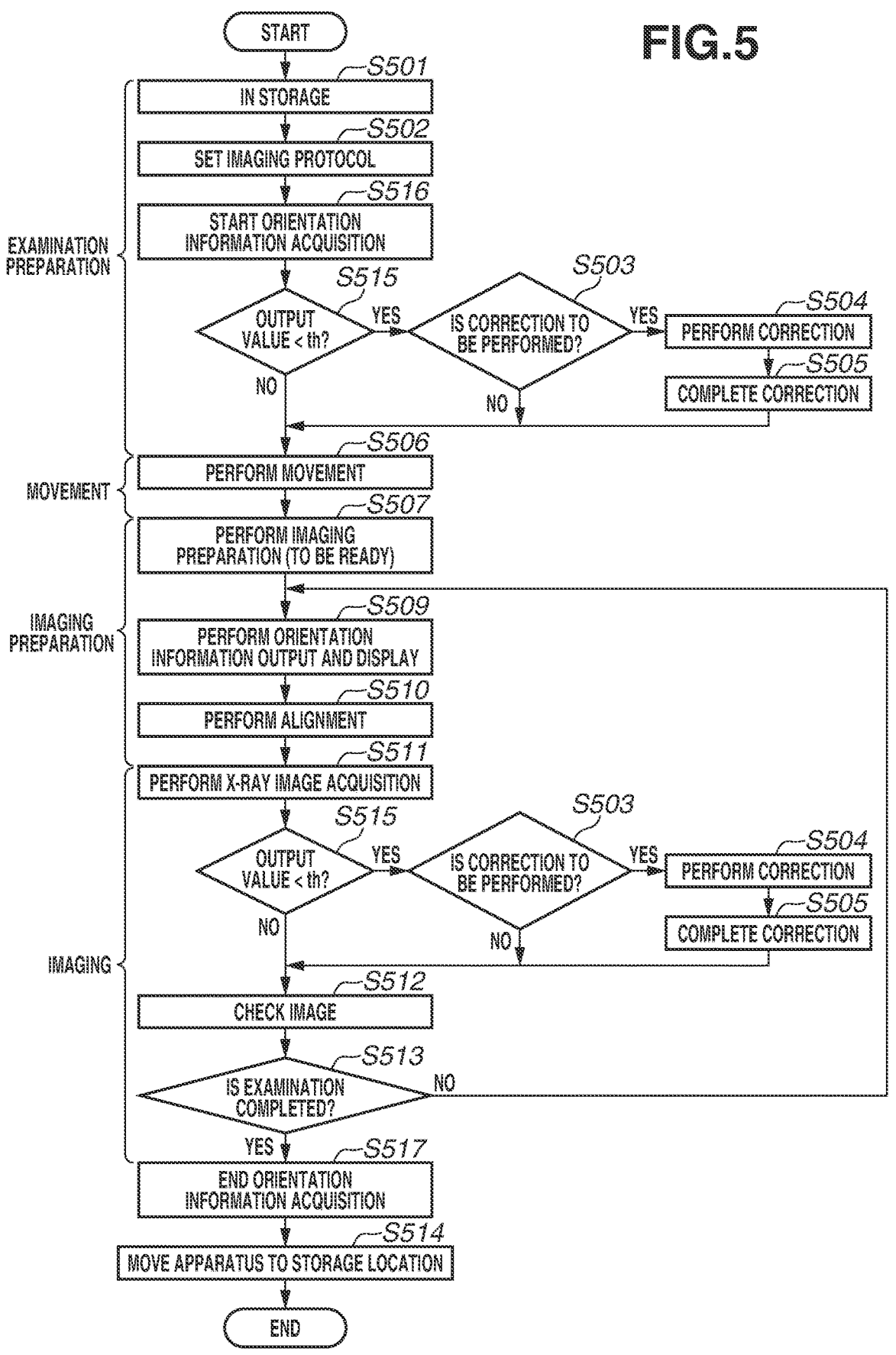
FIG. 5 is a flowchart illustrating an examination flow according to a third exemplary embodiment.

Next, an examination flow of calculating positional information based on the outputs of the acceleration sensor, aligning the radiographic imaging apparatus and the radiation generating apparatus with each other, and performing radiographic imaging will be described below with reference to FIG. 5. Redundant descriptions of each step that corresponds to a step according to the first or second exemplary embodiment are omitted.

The state of being in storage at the charging apparatus in step 501 is defined as the initial position. At the timing of the protocol setting in step 502, the acceleration sensor starts acquiring data (step 516). Next, the determination of whether to perform the correction is performed in step 503. Since the corresponding step according to the first and second exemplary embodiments is described above, redundant descriptions thereof are omitted. Thereafter, the radiographic imaging apparatus is moved, and the imaging preparation is performed.

While angle information about the radiographic imaging apparatus 104 is output for the alignment in the above-described methods according to the first and second exemplary embodiment, a movement amount (coordinates) from the initial position is output according to the present exemplary embodiment, and the alignment with the radiation generating apparatus 101 is performed. As a method for the alignment, positional information (coordinates) about the radiation generating apparatus 101 and positional information (coordinates) about the radiographic imaging apparatus 104 can be output to the control PC to determine the distance between the radiation generating apparatus 101 and the radiographic imaging apparatus 104, and the positions can be adjusted manually. Further, the radiation generating apparatus 101 can be provided with a mechanism that enables automatic movement of the tube, and the alignment of the radiation generating apparatus 101 can be performed automatically based on the position (coordinate) of the radiographic imaging apparatus 104 so that the tube is positioned as appropriate.

Further, information displayed on, for example, the control PC can be changed from coordinate information to angle information to arrange the radiation generating apparatus and the radiographic imaging apparatus at desired angles after the positions (distance) of the radiation generating apparatus and the radiographic imaging apparatus are adjusted.

After the alignment in step 510 is completed, the radiographic image acquisition in step 511 is performed, and the processing proceeds to the determination of whether to perform the correction (step 503), the image check (step 512), and the end of the examination (step 513).

After all the examinations are ended, the orientation information acquisition by the acceleration sensor is ended (step 517), and the radiographic imaging apparatus is returned to the storage location (step 514). Then, the examination ends.

In a case where the correction of the output values of the orientation measurement unit 106 is performed at any one of the above-described timings, the offset components contained in the outputs of the acceleration sensor are removed, and the accuracy of the positional information calculation using the outputs of the acceleration sensor is enhanced.

Since the acceleration sensor continuously acquires orientation information from the examination preparation to the end of the examination, the positional information calculation load is heavy compared to the first and second exemplary embodiments. Thus, the positional information calculation can be performed not only by a computation unit in the radiographic imaging apparatus but also on the control PC 103.

Further, the offset components contained in the data may change before and after the correction of the output values of the orientation measurement unit 106 is performed. Thus, in order to further enhance the accuracy of the positional information calculation, the output data before the correction is performed can also be processed by the computation unit or on the control PC 103 to reduce the offset components in calculating positional information.

Other Exemplary Embodiments

The present invention can be realized also by a process in which a program configured to realize the above-described functions is supplied to a system or an apparatus via a network or a storage medium and one or more processors of a computer of the system or the apparatus read the program and execute the read program.

Further, various recording mediums can be used such as flexible disks, optical disks (e.g., compact disk read-only memory (CD-ROM), digital versatile disk read-only memory (DVD-ROM)), magneto-optical disks, magnetic tapes, non-volatile memories (e.g., universal serial bus (USB) memory), and read-only memories (ROMs). Further, the program configured to perform the above-described functions can be downloaded via a network, and a computer can execute the downloaded program.

Further, the case where the functions of the above-described exemplary embodiments are realized by executing the program codes read by the computer is not a limiting case. A case where an operating system (OS) running on the computer performs part of actual processing or the entire actual processing based on instructions of the program codes and the processing realizes the functions of the above-described exemplary embodiments is also encompassed.

Furthermore, the program codes read from the recording medium can be written to a memory of a function expansion board inserted in the computer or a function expansion unit connected to the computer. A case where a CPU of the function expansion board or the function expansion unit can perform part of the actual processing or the entire actual processing based on the instructions of the program codes and the processing realizes the above-described functions is also encompassed.

The present invention is not limited to the above embodiments and various changes and modifications can be made within the spirit and scope of the present invention. Therefore, to apprise the public of the scope of the present invention, the following claims are made.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention makes it possible to enhance accuracy of alignment of a radiation generating apparatus and a radiographic imaging apparatus with each other by correcting output values that are output from an acceleration sensor or a gyro sensor used as an orientation measurement unit of the radiographic imaging apparatus and contain errors.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiographic imaging apparatus comprising:
an orientation measurement unit configured to measure information about an orientation of the radiographic imaging apparatus,
wherein the orientation measurement unit, based on receiving, via communication, an input of a setting of an imaging protocol, confirms an output value relating to the orientation, and performs an offset correction of the output value of the orientation measurement unit based on confirming that the output value corresponds to a stationary state of the radiographic imaging apparatus.

2. The radiographic imaging apparatus according to claim 1, wherein the orientation measurement unit performs the correction in a case where the radiographic imaging apparatus is stationary.

3. The radiographic imaging apparatus according to claim 2, further comprising a control unit configured to perform control to perform radiographic imaging using the radiographic imaging apparatus,
wherein the orientation measurement unit performs the correction in a case where the control unit detects the radiographic imaging apparatus being stationary.

4. The radiographic imaging apparatus according to claim 3,
wherein the control unit has a plurality of operation modes, and
wherein the orientation measurement unit performs the correction based on one of the plurality of operation modes.

5. A radiographic imaging apparatus comprising:
a photoelectric conversion element configured to convert light based on radiation into charge;
a control unit configured to perform control to perform radiographic imaging using the radiographic imaging apparatus, the control unit having a plurality of operation modes including an operation mode in which the photoelectric conversion element is not driven; and an orientation measurement unit configured to measure information about an orientation of the radiographic imaging apparatus, wherein the orientation measurement unit performs correction of an output value of the orientation measurement unit in a case where an imaging protocol is set for the radiographic imaging apparatus during the operation mode in which the photoelectric conversion element is not driven.

6. A radiographic imaging apparatus comprising:

a photoelectric conversion element configured to convert light based on radiation into charge;

a control unit configured to perform control to perform radiographic imaging using the radiographic imaging apparatus, the control unit having a plurality of operation modes; and an orientation measurement unit configured to measure information about an orientation of the radiographic imaging apparatus, wherein the orientation measurement unit performs correction of an output value of the orientation measurement unit in a case where, after the radiographic imaging apparatus is irradiated and imaging of a radiographic image is performed, a transition is made to a mode of driving the photoelectric conversion element and awaiting an irradiation permission signal.

7. The radiographic imaging apparatus according to claim 2, wherein the orientation measurement unit performs the correction in a case where the radiographic imaging apparatus is detected as being stationary based on the output value.

8. The radiographic imaging apparatus according to claim 3, wherein the control unit performs a calculation on the orientation of the radiographic imaging apparatus based on the output value, and wherein the orientation measurement unit performs the correction in a case where a differential value of the output value calculated by the control unit is less than a predetermined threshold.

9. The radiographic imaging apparatus according to claim 8, wherein the orientation measurement unit performs the correction by subtracting the differential value from the output value.

10. The radiographic imaging apparatus according to claim 3, wherein the orientation measurement unit performs the correction based on a pre-stored known orientation of the radiographic imaging apparatus stabilized at a predetermined position and a current orientation of the radiographic imaging apparatus that is calculated by the control unit.

11. The radiographic imaging apparatus according to claim 10, wherein the orientation measurement unit performs the correction in a case where the radiographic imaging apparatus is detected as being stationary based on the known orientation and the current orientation.

12. The radiographic imaging apparatus according to claim 10, wherein the control unit calculates a movement amount of the radiographic imaging apparatus from the known orientation based on the known orientation and the output value.

13. A radiographic imaging system comprising:

a radiographic imaging apparatus according to claim 1; and a radiation generating apparatus configured to emit radiation to the radiographic imaging apparatus to perform radiographic imaging.

14. A method for controlling a radiographic imaging apparatus, the method comprising:

measuring information about an orientation of the radiographic imaging apparatus;

receiving, via communication, an input of a setting of an imaging protocol;

confirming an output value relating to the orientation from an orientation measurement unit based on a-the receiving; and performing an offset correction of the output value based on confirming that the output value corresponds to a stationary state of the radiographic imaging apparatus.

15. The method for controlling the radiographic imaging apparatus according to claim 14, further comprising:

detecting whether the radiographic imaging apparatus is stationary; and performing the offset correction based on the detecting.

16. A non-transitory computer-readable recording medium that records a program that causes a computer to perform the control method according to claim 15.

* * * * *